(12) United States Patent
Verkruijsse et al.

(10) Patent No.: US 11,033,189 B2
(45) Date of Patent: Jun. 15, 2021

(54) WEARABLE DEVICE AND SYSTEM FOR ACQUIRING PHYSIOLOGICAL INFORMATION OF A SUBJECT

(71) Applicant: KONINKLIJKE PHILIPS N.V., Eindhoven (NL)

(72) Inventors: Willem Verkruijsse, Veldhoven (NL); Ihor Olehovych Kirenko, Veldhoven (NL); Alexander Dubielczyk, Gaertringen (DE); Marcus Schwenk, Stuttgart (DE); Gerard De Haan, Helmond (NL)

(73) Assignee: KONINKLIJKE PHILIPS N.V, Eindhoven (NL)

( * ) Notice: Subject to any disclaimer, the term of this patent is extended or adjusted under 35 U.S.C. 154(b) by 324 days.

(21) Appl. No.: 15/777,252

(22) PCT Filed: Nov. 11, 2016

(86) PCT No.: PCT/EP2016/077378
§ 371 (c)(1),
(2) Date: May 18, 2018

(87) PCT Pub. No.: WO2017/089147
PCT Pub. Date: Jun. 1, 2017

(65) Prior Publication Data
US 2018/0333053 A1    Nov. 22, 2018

(30) Foreign Application Priority Data

Nov. 24, 2015 (EP) .................................. 15195949

(51) Int. Cl.
*A61B 5/1455* (2006.01)
*A61B 5/00* (2006.01)
(Continued)

(52) U.S. Cl.
CPC .......... *A61B 5/0077* (2013.01); *A61B 5/0295* (2013.01); *A61B 5/02427* (2013.01);
(Continued)

(58) Field of Classification Search
None
See application file for complete search history.

(56) References Cited

U.S. PATENT DOCUMENTS

| 7,894,644 B2 | 2/2011 | Padinger |
| 2003/0090650 A1 | 5/2003 | Fujieda |

(Continued)

FOREIGN PATENT DOCUMENTS

JP    2013009709    1/2013

OTHER PUBLICATIONS

Verkruysse et al., "Remote plethysmographic imaging using ambient light", Optics Express, 16(26), Dec. 22, 2008, pp. 21434-21445.

*Primary Examiner* — Eric F Winakur
*Assistant Examiner* — Marjan Fardanesh (57) ABSTRACT

The present invention relates to a wearable device for acquiring physiological information of a subject. To combine the advantages of a contact sensor and a contactless sensor, the wearable device comprises an optical emitter (10) for emitting light into the subject's skin, an optical sensor (20) for receiving light scattered back from the subject's skin in response to the emission of light into the subject's skin, the received light representing or allowing the derivation of physiological information of the subject, and a carrier (30) for being held at the subject's skin and for carrying said emitter (10) and said sensor (20) such that a light receiving area (12), at which the emitted light enters the subject's skin, substantially corresponds to a light reflecting area (22), at which at least part of the scattered light leaves the subject's skin and is received by said optical sensor, the
(Continued)

optical sensor (20) is arranged between the optical emitter (10) and the light receiving area (12) and is at least partially transparent for the light emitted by the optical emitter or the optical sensor (10) is arranged between the optical sensor (20) and the light reflecting area (22) and is at least partially transparent for the light reflected from the light reflecting area.

11 Claims, 4 Drawing Sheets

(51) Int. Cl.
*A61B 5/024* (2006.01)
*A61B 5/0295* (2006.01)
*A61B 5/0205* (2006.01)

(52) U.S. Cl.
CPC ...... *A61B 5/14552* (2013.01); *A61B 5/14558* (2013.01); *A61B 5/681* (2013.01); *A61B 5/6813* (2013.01); *A61B 5/0205* (2013.01); *A61B 5/6831* (2013.01); *A61B 2562/0238* (2013.01); *A61B 2562/043* (2013.01); *A61B 2562/046* (2013.01); *A61B 2562/063* (2013.01); *A61B 2562/066* (2013.01); *A61B 2562/146* (2013.01)

(56) References Cited

U.S. PATENT DOCUMENTS

| | | |
|---|---|---|
| 2007/0270666 A1 | 11/2007 | Amano |
| 2009/0112071 A1 | 4/2009 | Leboeuf |
| 2013/0060104 A1 | 3/2013 | Schlottau |
| 2013/0261415 A1 | 10/2013 | Ashe |
| 2014/0051955 A1* | 2/2014 | Tiao ............... A61B 5/14552 600/323 |
| 2014/0276119 A1 | 9/2014 | Venkatraman |
| 2014/0343383 A1 | 11/2014 | Sato |
| 2015/0216484 A1 | 8/2015 | Kasahara |

* cited by examiner

WEARABLE DEVICE AND SYSTEM FOR ACQUIRING PHYSIOLOGICAL INFORMATION OF A SUBJECT

CROSS REFERENCE TO RELATED APPLICATIONS

This application is the U.S. National Phase application under 35 U.S.C. § 371 of International Application No. PCT/EP2016/077378, filed Nov. 11, 2016, published as WO 2017/089147 on Jun. 1, 2017, which claims the benefit of European Patent Application Number 15195949.1 filed Nov. 24, 2015. These applications are hereby incorporated by reference herein.

FIELD OF THE INVENTION

The present invention relates to a wearable device for acquiring physiological information of a subject, such as a patient, sportsperson, elderly person, baby, or a person in general. The present invention relates further to a corresponding system for acquiring physiological information of a subject.

BACKGROUND OF THE INVENTION

Vital signs of a person, for example the heart rate (HR), the respiration rate (RR) or the arterial blood oxygen saturation measured by pulse oximetry (SpO2), serve as indicators of the current health state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared in case of oxygen saturation) and applying photometric measurement principles e.g. the blood oxygen saturation or other blood and tissue constituent concentrations can be determined. Different kinds of such contact sensors (also called wearable devices) are commonly known and used, including contact finger pulse oximeters, contact forehead pulse oximeter sensors, contact pulse sensors, etc.

Recently, non-contact, remote photoplethysmography (rPPG) devices (also called camera-based PPG devices) for unobtrusive measurements have been described in many publications, e.g. in Verkruysse et al., "Remote plethysmographic imaging using ambient light", Optics Express, 16(26), 22 Dec. 2008, pp. 21434-21445, which demonstrates that photoplethysmographic signals can be measured remotely using ambient light and a conventional consumer level video camera, using red, green and blue color channels.

Remote PPG utilizes light sources or, in general radiation sources, disposed remotely from the subject of interest. Similarly, also a detector, e.g., a camera or a photo detector, can be disposed remotely from the subject of interest, i.e. without contact to the subject. Therefore, remote photoplethysmographic systems and devices are considered unobtrusive and well suited for medical as well as non-medical everyday applications. This technology particularly has distinct advantages for patients with extreme skin sensitivity requiring vital signs monitoring such as Neonatal Intensive Care Unit (NICU) patients with extremely fragile skin or premature babies.

Recently, much progress has been achieved in improving the motion robustness of camera-based remote PPG. Essentially this progress was enabled by exploiting massive parallel sensing using a 2D image array and the use of multiple wavelengths. In ambulant patient monitoring, however, wearable sensors are often more practical as patients may easily leave the field of view of a camera. Further, camera-based remote PPG enables measuring at very different locations at the body with a single calibration function while conventional pulse oximeters need to have calibration functions that are specific for the combination of optical properties of the tissue at the measurement site, the opto-mechanical sensor design and the pressure applied to the tissue. These dependencies have been the reason for the problem to get reproducible results with conventional pulse oximeters when being used at otherwise attractive application sites, like e.g. wrist, arm or thorax.

The contact PPG signal has a much higher strength than a camera-based PPG signal. The strong resulting SNR of the signal can be explained by a relatively large penetration depth of the dedicated light and the fact that almost all the light sensed by the light detector has 'seen'/travelled through the skin with pulsatile blood vessels. This is obtained by placing light source and detector at a relatively large distance, regardless whether reflective or transmissive PPG is exploited.

However, the motion robustness of these contact sensors currently is rather limited. This is because the contact PPG measurement (transmissive or reflective) relies on a well-defined light path through the skin, which however, is heavily influenced by motion.

The signals from an accelerometer embedded in the device can be used to some extent to compensate for such motion artifacts in the PPG signal; however, this is much inferior to the motion robustness obtained by camera-based systems where the compensating signals are obtained from similar (optical) sources instead of the completely different accelerometer modality.

Also, as camera based oximetry mainly utilizes signal information from the more homogeneous shallow skin layers, its calibration function has weaker dependencies on the measurement location at the body. This is especially true for locations with significant large vessel structures in deeper tissue layers which are therefore typically ruled out for conventional pulse oximetry measurements.

US 2009/0112071 A1 discloses methods and apparatus for qualifying and quantifying excitation-dependent physiological information extracted from wearable sensors in the midst of interference from unwanted sources are provided. An organism is interrogated with at least one excitation energy, energy response signals from two or more distinct physiological regions are sensed, and these signals are processed to generate an extracted signal. The extracted signal is compared with a physiological model to qualify and/or quantify a physiological property. Additionally, important physiological information can be qualified and quantified by comparing the excitation wavelength-dependent response, measured via wearable sensors, with a physiological mode.

JP 2013/009709 A discloses a biosensor including a board that has optical transparency, the light emitting element that is provided on a mounting face side of the board and emits light, and the light receiving element that is provided on a non-mounting face side of the board and receives reflected light from a living body among the light emitted from light emitting element to output a signal corresponding to the light reception. The light receiving element is provided for the board on its non-mounting surface side opposite to the mounting surface side where the light emitting element is provided, and is set back from a light emitting surface at a distance equal to or more than the thickness of the board.

US 2015/0216484 A1 discloses a biological information processing apparatus comprises a body motion detection unit that detects a body motion of a subject. A measurement method selection unit selects one measurement method on the basis of a detection result from the body motion detection unit, from among a plurality of measurement methods of measuring a blood glucose level by applying irradiation waves toward a living body of the subject.

SUMMARY OF THE INVENTION

It is an object of the present invention to provide a wearable device and a corresponding system for acquiring physiological information of a subject, in particular physiological information which represents or may be used for deriving a vital sign of a subject, by which some advantages of the camera-based PPG system can be achieved.

According to one aspect of the present invention a wearable device is presented comprising
an optical emitter for emitting light into the subject's skin,
an optical sensor for receiving light scattered back from the subject's skin in response to the emission of light into the subject's skin, the received light representing or allowing the derivation of physiological information of the subject, and
a carrier for being held at the subject's skin and for carrying said emitter and said sensor such that a light receiving area, at which the emitted light enters the subject's skin, substantially corresponds to a light reflecting area, at which at least part of the scattered light leaves the subject's skin and is received by said optical sensor,
wherein the optical sensor is arranged between the optical emitter and the light receiving area and is at least partially transparent for the light emitted by the optical emitter or the optical emitter is arranged between the optical sensor and the light reflecting area and is at least partially transparent for the light reflected from the light reflecting area.

According to another aspect of the present invention a system is presented comprising
a wearable device as disclosed herein and
a processing unit for deriving physiological information of the subject from the light scattered back from the subject's skin and received by the wearable device, in particular by evaluating the time-varying amplitude of the received light.

The present invention is based on the idea to obtain at lease some advantages of a remote PPG device or system by reducing the optical path-length between the light source (i.e. the optical emitter) and the light detector (i.e. the optical sensor). This reduces the influence of motion and the calibration dependency on the measurement location at the body. The proposed relative arrangement and configuration of the optical emitter and the optical sensor resembles closely the case of camera-based PPG measurement, where the skin is sensed at the same spot where it is illuminated. In other words, the light receiving area, which is illuminated by the emitted light, substantially coincides with the light reflecting area, from which scattered light leaves the skin and from which said scattered light is sensed by the optical sensor. Hereby, the light receiving area and the light reflecting area may have different sizes, but they substantially overlap. For instance, the light reflecting area may be fully covered by the light receiving area. Further, in contrast with a camera-based approach, the specular reflection from the skin can be eliminated by the proposed wearable device due to the direct contact or the very short distance of the optical sensor with the skin.

The optical sensor is arranged between the optical emitter and the light receiving area and is at least partially transparent for the light emitted by the optical emitter or the optical emitter is arranged between the optical sensor and the light reflecting area and is at least partially transparent for the light reflected from the light reflecting area. The optical sensor and the optical emitter are thus stacked upon each other and hence require less space in a lateral direction. A homogeneous illumination of the receiving area of the skin can thus be achieved.

There are different embodiments possible for implementing the optical emitter and the optical sensor. According to an embodiment said optical sensor comprises an array (one-dimensional or two-dimensional) of a plurality of single-pixel sensor elements, wherein preferably two or more sensor elements have a different spectral sensitivity. The use of a plurality of sensor elements and of an average of the sensor signals acquired by some or all sensor elements for evaluation provides spatial redundancy, e.g. in order to improve motion robustness. Using sensor signals in different spectral ranges allows deriving certain blood and tissue constituent concentrations, such as SpO2 as commonly known in the art of PPG.

Alternatively, said optical sensor may comprise a two-dimensional optical sensor, e.g. be a camera or photodetector array, or a single sensor element, e.g. a photosensor. Such an embodiment may require fewer readout channels for reading out the sensor signal(s) and less processing efforts for deriving a vital sign from the acquired sensor signals.

Similarly, the optical emitter may comprise a plurality of emitter elements, wherein preferably two or more emitter elements have a different emission spectrum allowing the derivation of certain blood and tissue constituent concentrations, like SpO2, from the acquired sensor signals, which are evaluated in the desired wavelength channels. In an embodiment multiple sensor-emitters pairs may be used, all with substantially zero minimal path-lengths, which provides for some motion robustness.

Alternatively, said optical emitter comprises a single emitter element, reducing the efforts for controlling the optical emitter and the required space.

In an embodiment the wearable device may further comprise an optical filter in the light path between the optical emitter and the optical sensor, which is configured to filter the emitted and/or the reflected light. By use of such a filter the spectrum of the emitted and/or received light can be changed so that neither the optical emitter nor the optical sensor needs to be configured emit or sense certain spectral ranges.

For the relative arrangement of optical emitter and optical sensor various advantageous possibilities exist. In a preferred embodiment said optical emitter comprises an illumination layer arranged between the optical sensor and the light reflecting area and one or more emitter elements arranged outside the light path between the reflecting area and the optical sensor such that emitted light is coupled into the illumination layer, wherein said illumination layer is configured to use the emitted light coupled into the illumination layer to illuminate the light receiving area and to transmit light reflected from the reflecting area to the optical sensor. In this way a side-lit arrangement may be achieved, in which the light is transmitted into the illumination layer preferably from a front face at one or more of its sides, which is then, preferably in a uniform fashion, illuminating the receiving area. This provides the advantage of a simple mechanical arrangement to provide a uniform and efficient illumination.

In other embodiments the optical sensor is arranged between the optical emitter and the light receiving area and is at least partially transparent for the light emitted by the optical emitter or the optical emitter is arranged between the optical sensor and the light reflecting area and is at least partially transparent for the light reflected from the light reflecting area. In these embodiments the optical sensor and the optical emitter are stacked upon each other and hence require less space in a lateral direction. Also with these embodiments a homogeneous illumination of the receiving area of the skin can be achieved.

Still further, in an embodiment the optical emitter comprises an array of a plurality of emitter elements and the optical sensor comprises an array of a plurality of sensor elements.

The wearable device may further comprise a polarizer in the optical path between the light reflecting area and the optical sensor for suppressing specular reflections from the skin. This improves the SNR of the acquired sensor signals and hence of the derived vital sign(s).

The carrier may be configured to allow direct contact of the optical sensor, the optical emitter and/or at least part of the carrier, in particular outside of the light reflecting area, with the skin. It is not mandatory that the optical emitter and/or the optical sensor have direct contact. Having a short distance (e.g. a few mm) is also possible, as long as the skin can be sufficiently illuminated and the sensor signal can be sufficiently acquired; for instance, the thickness of the illumination layer (or an optical light-guide) may determine said distance, and further, the practical limitations for a wearable may provide an upper limit for said distance, but these are not really absolute limits for the maximum distance. When the wearable device only makes contact with the skin in a region outside the reflecting area of the skin it can be prevented that motion of the subject affects the physiological information derived from said area.

The obtained physiological information is preferably derived from blood-volume variations in the skin (i.e. using the above described photoplethysmography (PPG) technique) and concerns vital signs, like pulse, respiratory signal, blood oxygenation, etc. This processing may be performed in the wearable device itself, e.g. a processor provided in the wearable device, or in a different entity of the proposed system, in particular the processing unit of the system. The processing unit may thereby be a computer, processor, workstation, a laptop, a smartphone, a patient monitor, etc., which may be provided at the subject, a user (e.g. caregiver), a doctor, etc. From the light received by the optical sensor one or more digital signal(s) (also called sensor signal(s) herein) are preferably generated, and the time-varying amplitude of said sensor signal(s) is preferably evaluated as conventionally known from photoplethysmography.

In a practical implementation the sensor signal representing the time-varying light reflected from the skin at a first location is compared to or combined with a sensor signal representing the time-varying light reflected from a second location to extract the physiological information. This embodiment provides spatial redundancy e.g. to improve motion robustness.

In another practical implementation the sensor signal representing the time-varying light reflected from the skin in a first part of the spectrum is combined with a sensor signal representing the time-varying light reflected from a second part of the spectrum to extract the physiological information, i.e. different wavelength intervals are used, e.g. to improve motion robustness, or to extract physiological information like SpO2 values.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Figure 1A:
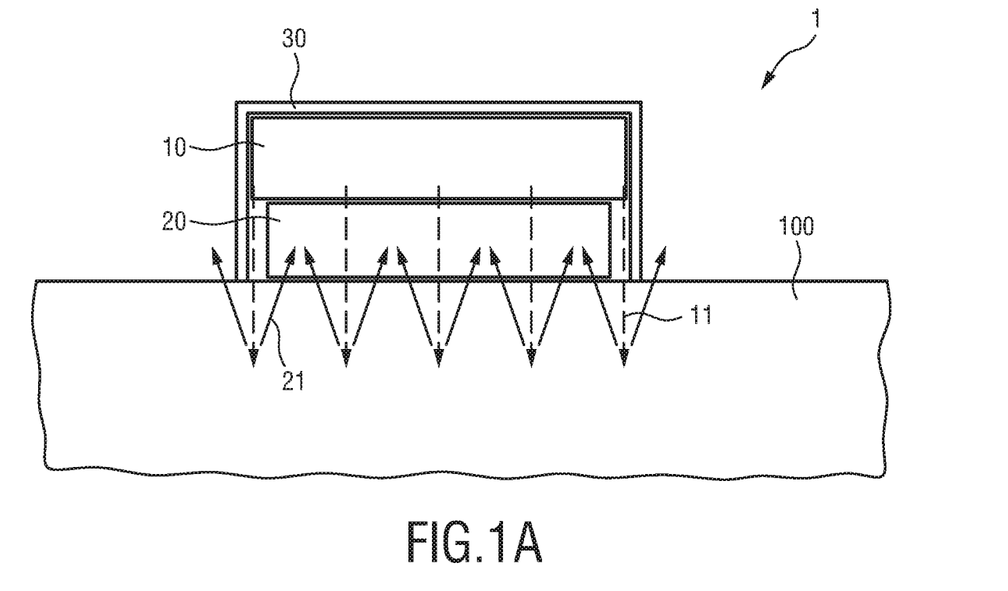
FIG. 1 shows a schematic diagram of a first embodiment of a wearable device according to the present invention.
Figure 1B:
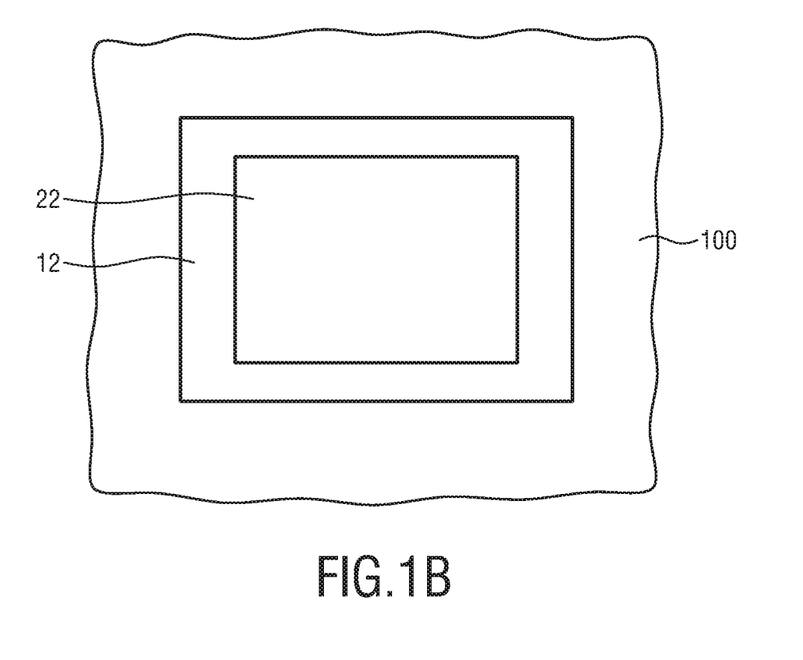

FIG. 1 shows a schematic diagram of a first embodiment of a wearable device according to the present invention, wherein FIG. 1A shows a cross-sectional view of the wearable device 1 and FIG. 1B shows a top view of the skin region in which the wearable device 1 may be mounted. The wearable device 1 comprises an optical emitter 10 for emitting light 11 into the subject's skin 100 and an optical sensor 20 for receiving light 21 scattered back from the subject's skin 100 in response to the emission of light into the subject's skin 100. In use, the wearable device 1 is mounted to the subject's skin 100, e.g. by use of a sticker or a belt, for instance at the finger, wrist, chest, forehead, etc. Such a wearable device 1 is generally used for obtaining a vital sign of the subject, such as the heart rate, respiration rate, SpO2, etc. For this purpose the received light (representing a sensor signal or a PPG signal) is evaluated, which represents or allows the derivation of physiological information of the subject.

The wearable device 1 further comprises a carrier 30 for being held at the subject's skin 100 and for carrying said emitter 10 and said sensor 20 such that a light receiving area 12, at which the emitted light 11 enters the subject's skin 100, substantially corresponds to a light reflecting area 22, at which at least part of the scattered light 21 leaves the subject's skin 100 and is received by said sensor 20. In other words, the shortest light path for the light travelling through the subject's skin to the optical sensor 20 is substantially zero. The carrier 30 may e.g. be a substrate, PCB, housing, wristband, snap-on mounting or even a flexible holder such as a rubber strap holding the emitter 10 and the sensor 20 and allowing the mounting of the wearable device 1 to a desired body part of the subject such that the emitter 10 and/or the sensor 20 are in contact with the skin or in very close proximity to the skin.

The main idea is to combine the advantages of conventional contact and camera-based contactless monitoring of PPG signals. The contact PPG measurement (transmissive or reflective) relies on a controlled light path through the skin area resulting in a relatively large pulsatility (amplitude of AC signal) of the measured PPG signal. Such strong SNR of the signal can be explained by a relatively large penetration depth of the dedicated light and the fact that almost all the light sensed by the light detector has 'seen'/travelled through the skin with pulsatile blood vessels. The contactless PPG measurement does not rely on a specific controlled light path through the skin area, but rather acquires the signal reflected from relatively large spatial area, from an effectively much shallower depth. As a result, the amplitude of the PPG signal acquired in a contactless mode is much smaller than the amplitude of contact PPG probe, because the longer the length which light travels through the skin before being reflected as diffuse light, the more is its intensity modulated by pulsatile blood vessels through absorption.

The embodiment of the wearable sensor 1 shown in FIG. 1 may use as optical sensor 20 a single sensor element, or a 2D optical sensor, or a 2D array of sensor elements. The light emitter 10 (also called illumination unit or light source) and the optical sensor 20 are placed in such way that the sensor 20 obtains light 21 uniformly emitted into the receiving area 12 of the skin 100 and reflected from reflecting area 22 of the skin 100. Moreover, the sensor 20 obtains the light, which comes from various parts of the light emitter 10, thus no single optical path through the skin area occurs and all the advantages of non-contact camera PPG sensing are exploited. Since the sensed area of skin (i.e. the reflecting area 22) is also illuminated, the shortest light-path through the skin 100 is substantially zero.

Figure 2A:
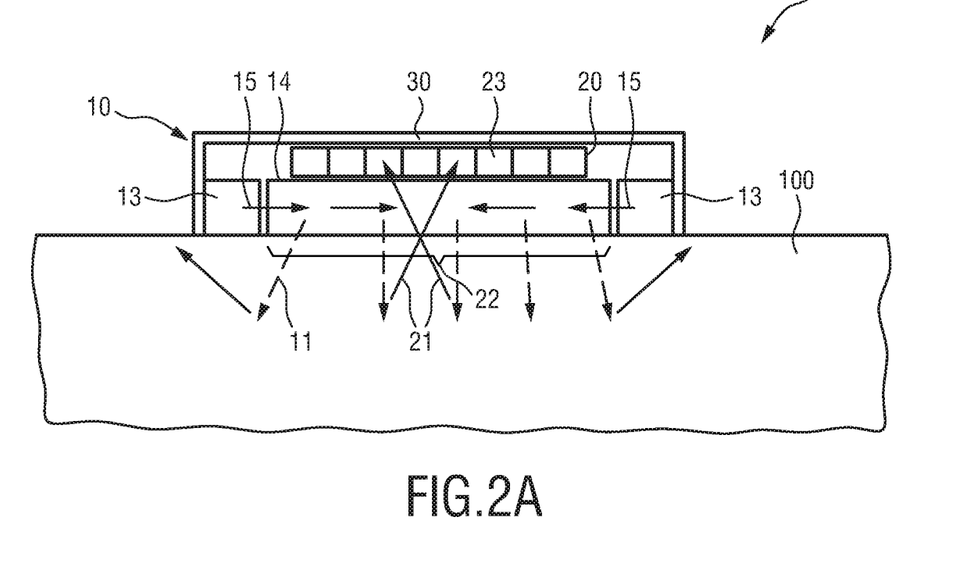
FIG. 2 shows a schematic diagram of a second embodiment of a wearable device according to the present invention.
Figure 2B:
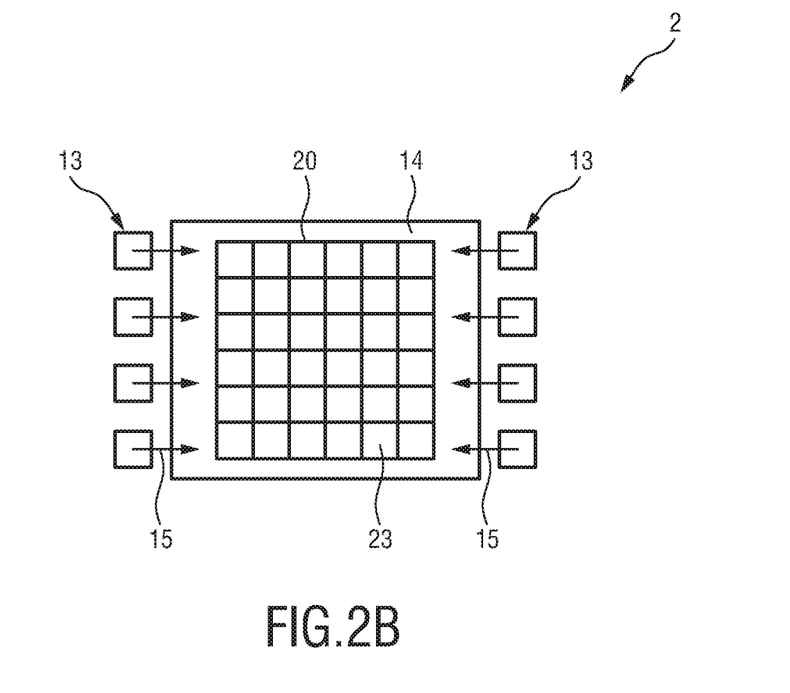

FIG. 2 shows a schematic diagram of a second embodiment of a wearable device 2 according to the present invention, wherein FIG. 2A shows a cross-sectional view of the wearable device 2 and FIG. 2B shows a top view of the wearable device 2. In this embodiment the wearable device 2 is designed in a way to simulate a wide field illumination. In this the remote camera geometry (wide field illumination, wide field detection, capturing as much light reflected from the reflecting area 22 as possible and from different (preferably all) depths). This geometry minimizes corner effects due to asymmetry, which results in the full use of spatial redundancy (all pixels) and light penetration depths to essentially the same extent as in the camera-based remote PPG geometry.

The wearable device 2 comprises a 2D optical sensor 20, e.g. a camera sensor or an array of sensor elements 23 (e.g. photodetectors), and a dedicated optical emitter 10. The emitter 10 in this embodiment comprises an illumination layer 14 arranged between the optical sensor 20 and the light reflecting area 22 and one or more emitter elements 13 arranged outside the light path between the reflecting area 22 and the optical sensor 20 such that emitted light 15 is coupled into the illumination layer 14.

The illumination layer 14 is generally configured to use the emitted light 15 coupled into the illumination layer 14 to illuminate the light receiving area 12 and to transmit light 21 reflected from the reflecting area 22 to the optical sensor 20. Preferably, the emitter elements 13 couple light of different wavelengths from a front face at one or more sides into the (side-lit) illumination layer 14 of refractive index close to that of skin. As a consequence, the illumination layer couples light preferentially into skin 100 due to high internal reflections. Diffusely reflected light 21 coming back from the reflecting area 22 skin will, by virtue of its angle, less internally reflected and pass through the illumination layer 14 towards the 2D sensor 20. Moreover, the light sensed by a specific sensor element 23 will be dominated by the light that has travelled the shortest distance through the skin 100, i.e. a substantially zero-distance.

The emitter elements 13 may be arranged around the complete illumination layer 14, i.e. may be provided at all sides. Instead a single light emitting element surrounding the illumination layer 14 may be used.

Optionally, an additional transmissive layer (not shown) having a low refractive index (n), e.g. a layer of air, is provided between the illumination layer 14 and the optical sensor 20 to optimize internal reflectance in the illumination layer 14 which has a higher refractive index.

Figure 3:
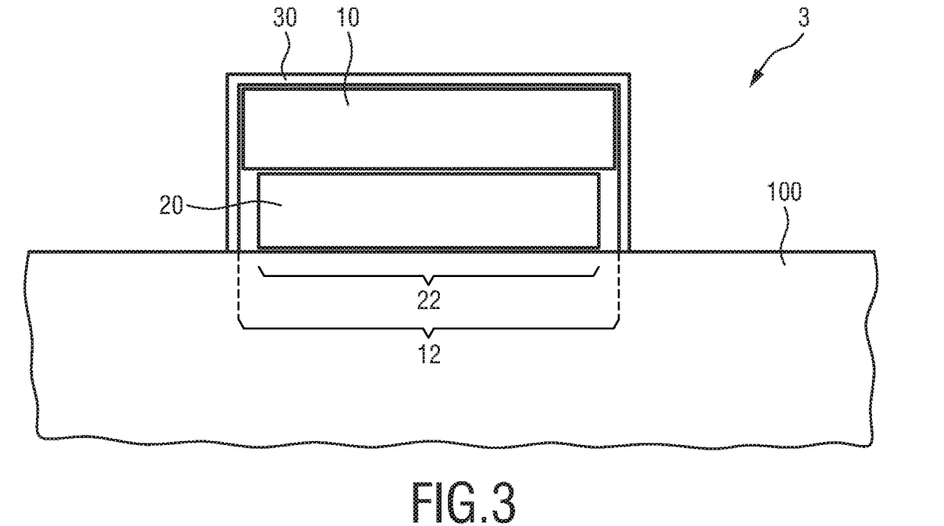
FIG. 3 shows a schematic diagram of a third embodiment of a wearable device according to the present invention.

FIG. 3 shows a schematic diagram of a third embodiment of a wearable device 3 according to the present invention. In this embodiment the optical sensor 20 is arranged between the optical emitter 10 and the light receiving area 12 and is at least partially transparent for the light 11 emitted by the optical emitter 10. Hereby, the optical sensor 20 may be a single image sensor, a single pixel detector, a discrete detector (e.g. a detector that has discrete locations that are transparent to allow the light of the emitter pass through these discrete transparencies), or an array of sensor elements. The optical emitter may similarly be a single emitter element, or an array of a plurality of emitter elements.

In an embodiment the optical emitter 10 emits light in a band of optical wavelengths between 400 nm and 1200 nm and the optical sensor 20 is sensing light in said band of optical wavelengths.

In a further embodiment, a single sensor element may be provided per wavelength in combination with multiple emitter elements, wherein the two or more emitter elements have a different emission spectrum.

Figure 4A:
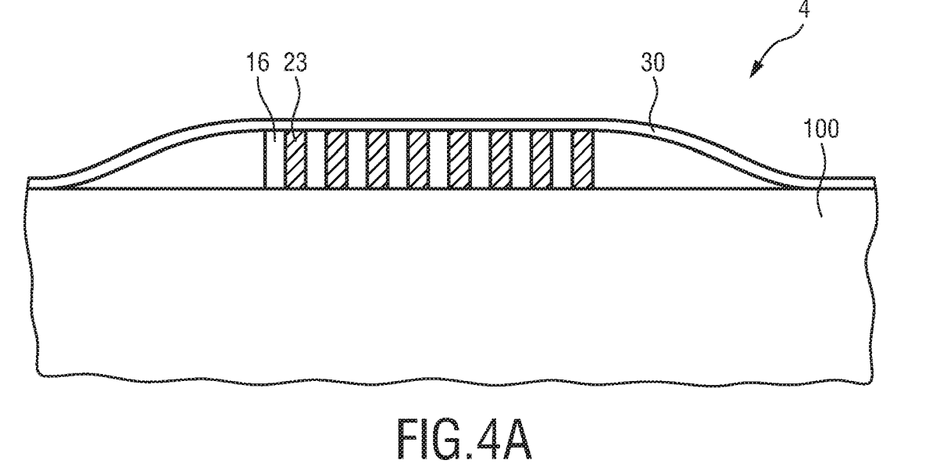
FIG. 4 shows a schematic diagram of a fourth embodiment of a wearable device.
Figure 4B:
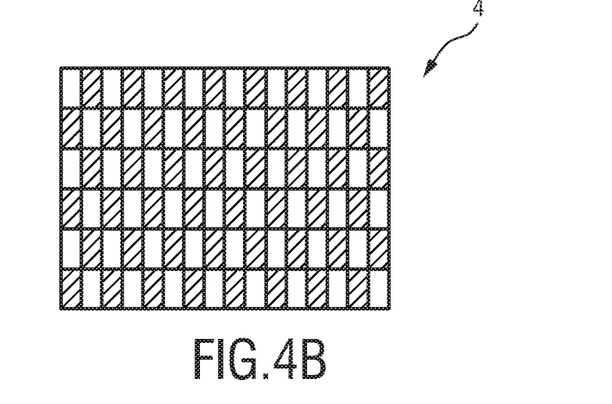

FIG. 4 shows a schematic diagram of a fourth embodiment of a wearable device 4, wherein FIG. 4A shows a cross-sectional view of the wearable device 4 and FIG. 4B shows a top view of the wearable device 4. In this embodiment the optical emitter 10 comprises an array of a plurality of emitter elements 16 and the optical sensor 20 comprises an array of a plurality of sensor elements 23 alternately arranged between single emitter elements 16 or groups of emitter elements 16. As another example of a carrier 30, a strap or band is shown in this embodiment, which may also be used in combination with other embodiments for carrying the emitter 10 and sensor 20 and, optionally, for holding the wearable device at the subject's body in certain applications.

Figure 5:
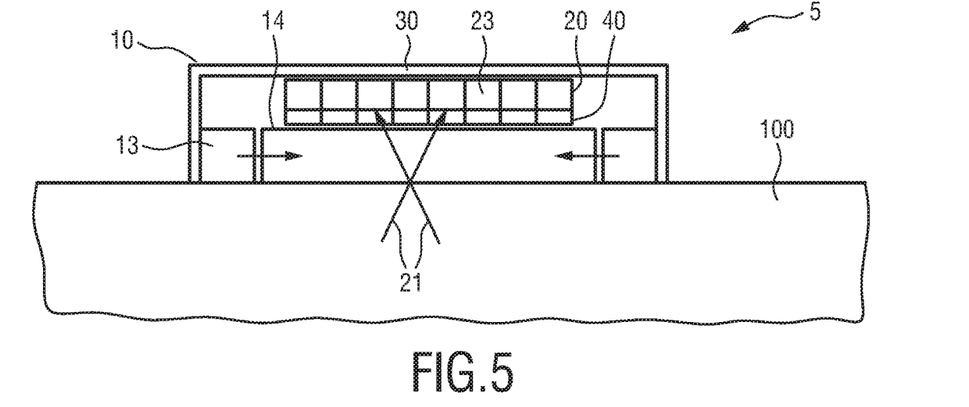
FIG. 5 shows a schematic diagram of a fifth embodiment of a wearable device according to the present invention.

FIG. 5 shows a schematic diagram of a fifth embodiment of a wearable device 5 according to the present invention. In this embodiment the light emitter 10 (emitter elements 13) produces illumination in a broad spectral range and one or more optical filters 40 are provided between the light reflecting area 22 and the optical sensor 20 to sample the reflected light 21, e.g. at several distinct wavelength ranges. For instance, different sensor elements 23 may be provided with different filters. Alternatively or in addition, filters may be provided in front of the optical emitter 10 (or separate emitter elements) to filter the emitted light.

This embodiment can be combined with either of the embodiments above and may comprise a 2D optical sensor (e.g. camera sensor) 20, and a dedicated broad-spectrum emitter 10 around the said 2D optical sensor to measure PPG signals in contact mode. The optical sensor 20 may be made 1D-wavelength selective using a grid, a prism, or simple pigment based filter-bands as filter(s) 40. The e.g. horizontal wavelength selectivity allows PPG detection for various vital signs including pulse, respiration, and SpO2, while the e.g. vertical redundancy of sensors allows for motion-robustness of all these signals. In a further embodiment, a Bayer filter pattern may be applied as filter 40 on the sensor array 20 to achieve different spectral sensitivity for individual sensor elements. In both embodiments the substantially zero-length of the shortest light path through the skin is preferably realized with a side-lit illumination layer 14 as described above, or one of the alternative embodiments.

Figure 6:
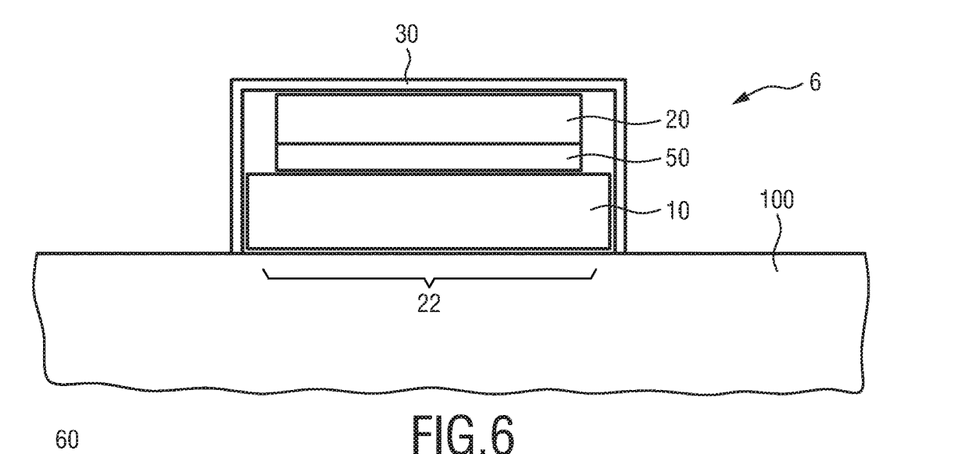
FIG. 6 shows a schematic diagram of a sixth embodiment of a wearable device according to the present invention.

FIG. 6 shows a schematic diagram of a sixth embodiment of a wearable device 6 according to the present invention. It comprises a polarizer 50 in the optical path between the light reflecting area 22 and the optical sensor 20 for suppressing specular reflections from the skin. The polarizer 50 may also be used in other embodiments of the wearable sensor.

Figure 7:
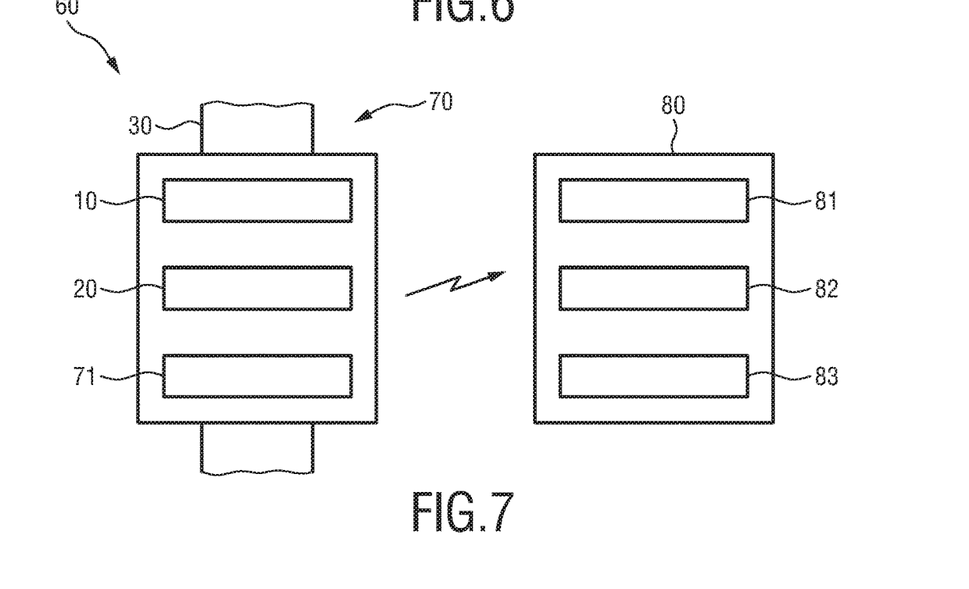
FIG. 7 shows a schematic diagram of a system according to the present invention.

A schematic diagram of a proposed system 60 is shown in FIG. 7. While generally the sensor signal(s) can be processed in the wearable device 70 (which can be configured as explained above and shown in anyone of FIGS. 1-6, in this embodiment the processing is performed in a processing unit 81, which is e.g. a processor and is preferably part of a separate entity 80, such as a smartphone, computer or patient monitor. The processing unit 81 preferably processes the sensor signals by evaluating the time-varying amplitude, as generally done in the art of PPG. From this processing physiological information, in particular one or more vital signs of the subject (e.g. heart rate, respiration rate, SpO2, etc.) can be obtained.

The wearable device 70 is hereby mounted to the subject's body, e.g. worn at the wrist by use of a wristband, clamped to the finger or ear lobe by use of a clamp, or mounted to the chest by use of a chest belt. The sensor signal(s) may be provided from the wearable device 70 to the processing unit 81 in a wired or wireless manner, e.g. through a direct cable, a wired network (e.g. LAN) or wireless communication (e.g. WLAN, Bluetooth, mobile communications network). Preferably, the wearable sensor may thus additionally comprise a transmitter 71 and the separate entity 80 may comprise a corresponding receiver 82. Further, a user interface 83 (e.g. a display) may be provided at the separate entity to output the resulting physiological information, e.g. the derived vital sign.

As explained above, various different options exist for the processing of the sensor signal, depending not only on the configuration and function of the wearable device, but also on the kind of physiological information (e.g. the kind of vital sign) that shall be obtained. In one option the light received by said optical sensor may be transformed into at least two digital signals corresponding to two spatially different locations of the light reflecting area. The at least two digital signals preferably correspond to two spatially different locations of the light reflecting area and are processed based on their time-varying amplitude. As mentioned above already, the same (or different) processing of the sensor signals can also be performed in the wearable device itself.

According to the present invention the shortest path of the light travelling through the skin is substantially zero. As a consequence the sensor signals will be dominated by the light from this shortest path and hence the thickness of the skin will play a relative small role compared to the known devices that employ a significant emitter-sensor distance. One application of the present invention is the improved measurement of pulse rate, respiration and SpO2 for patient monitoring. The monitoring, using a wearable device, is used ubiquitously in hospitals all over the world. Further applications include sports, elderly care, baby care, etc.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A wearable device for acquiring physiological information of a subject, said device comprising:
    an optical emitter for emitting light into the subject's skin,
    an optical sensor for receiving light scattered back from the subject's skin in response to the emission of light into the subject's skin, the received light representing or allowing the derivation of physiological information of the subject,
    a carrier for being held at the subject's skin and for carrying said emitter and said sensor such that a light receiving area, at which the emitted light enters the subject's skin, substantially corresponds to a light reflecting area, at which at least part of the scattered light leaves the subject's skin and is received by said optical sensor,
    wherein the optical emitter is arranged between the optical sensor and the light reflecting area and is at least partially transparent for the light reflected from the light reflecting area, and
    wherein said optical emitter comprises:
        an illumination layer arranged between the optical sensor and the light reflecting area; and
        one or more emitter elements arranged outside the light path between the reflecting area and the optical sensor such that emitted light is coupled into the illumination layer,
        wherein said illumination layer is configured to use the emitted light coupled into the illumination layer to illuminate the light receiving area and to transmit light reflected from the reflecting area to the optical sensor.

2. The wearable device according to claim 1, wherein said optical sensor comprises an array of a plurality of single-pixel sensor elements.

3. The wearable device according to claim 2, wherein two or more sensor elements have a different spectral sensitivity.

4. The wearable device according to claim 1, wherein said optical sensor comprises a two-dimensional optical sensor.

5. The wearable device according to claim 1, wherein said optical sensor comprises a single sensor element.

6. The wearable device according to claim 1, said optical emitter comprises a plurality of emitter elements.

7. The wearable device according to claim 6, wherein two or more emitter elements have a different emission spectrum.

8. The wearable device according to claim 1, said optical emitter comprises a single emitter element.

9. The wearable device according to claim 1, further comprising
an optical filter in the light path between the optical emitter and the optical sensor configured to filter the emitted and/or the reflected light, and/or
a polarizer in the optical path between the light reflecting area and the optical sensor for suppressing specular reflections from the skin.

10. The wearable device according to claim 1, wherein the carrier is configured to allow direct contact of the optical emitter and/or at least part of the carrier, in particular outside of the light reflecting area, with the skin.

11. A system for acquiring physiological information of a subject, said system comprising:
a wearable device as claimed in claim 1,
a processing unit for deriving physiological information of the subject from the light scattered back from the subject's skin and received by the wearable device.

* * * * *